US007001347B2

(12) United States Patent
Furuie

(10) Patent No.: US 7,001,347 B2
(45) Date of Patent: Feb. 21, 2006

(54) MASSAGE MACHINE

(75) Inventor: Yoshiya Furuie, Himeji (JP)

(73) Assignee: Sanyo Electric Co., Ltd., Moriguchi (JP)

( * ) Notice: Subject to any disclaimer, the term of this patent is extended or adjusted under 35 U.S.C. 154(b) by 97 days.

(21) Appl. No.: 10/743,332

(22) Filed: Dec. 23, 2003

(65) Prior Publication Data

US 2004/0186398 A1 Sep. 23, 2004

(30) Foreign Application Priority Data

Dec. 26, 2002 (JP) ............................ 2002-375985

(51) Int. Cl.
*A61F 19/00* (2006.01)

(52) U.S. Cl. .......................... 601/98; 610/99; 610/100

(58) Field of Classification Search .......... 601/97–103
See application file for complete search history.

(56) References Cited

U.S. PATENT DOCUMENTS 5,097,823 A * 3/1992 Kempler ..................... 601/111
5,792,080 A * 8/1998 Ookawa et al. ............. 601/115

FOREIGN PATENT DOCUMENTS

EP 1 048 281 A 11/2000
EP 1 210 927 A2 6/2002

* cited by examiner

*Primary Examiner*—Michael A. Brown
(74) *Attorney, Agent, or Firm*—Armstrong, Kratz, Quintos, Hanson & Brooks, LLP.

(57) ABSTRACT

The invention provides a massage machine wherein massage arms provided with kneading balls are held inclined forward to give a suitable massage. The massage machine comprises a kneading shaft (40) disposed on the massage unit (20) substantially horizontally, pivotal levers (33),(33) supported by the kneading shaft (40), massage arms (32),(32) supported by forward ends of the respective pivotal lever and kneading balls (31),(31) provided on the respective massage arms each at a position obliquely above the position where the massage arm is supported by the pivotal lever. An arm lock mechanism (80) is coupled to the massage unit for holding the kneading balls pushed out forward, and the arm lock mechanism tiltably supports arm lock rods (83),(83) each having one end connected to the massage arm at a position away from the position where the massage arm is supported by the pivotal lever. Each of the arm lock rods is forwardly tiltable by the arm lock mechanism to hold the massage arm with the kneading ball pushed out forward.

4 Claims, 7 Drawing Sheets

MASSAGE MACHINE

FIELD OF THE INVENTION

The present invention relates to massage machines of the chair type comprising kneading balls which can be held pushed out forward for massaging the person to be treated.

BACKGROUND OF THE INVENTION

Massage machines of the chair type are available which have a chair for a person to sit in to have his or her neck, shoulders, back or waist massaged.

The chair-type massage machine comprises a massage unit provided inside the backrest of the chair and movable upward and downward. The massage unit has a pair of opposite therapeutic fingers each comprising a massage arm bent at an obtuse angle and carrying a pair of kneading balls respectively at opposite ends thereof, and a pivotal arm for three-dimensionally moving the massage arm leftward, rightward, upward, downward, forward and rearward.

The massage arm is supported by the pivotal arm and biased by a spring so as not to freely rotate relative to the pivotal arm and to position the upper kneading ball as projected forward slightly beyond the lower kneading ball [see, for example, the publication of JP-A No. 2002-143253 (page 4, FIGS. 1 to 3)].

The chair-type massage machine has its backrest covered with a fabric cover or the like. It is likely that the fabric cover will be tensioned by the user leaning against the backrest. If the fabric cover is tensely stretched when a massage is to be given to the person, the massage arm is forced by the cover to stretch the spring when to be tilted, with the result that the massage arm is unable to incline, failing to deliver a sufficient therapeutic force to the person to be massaged.

Difficulties are encountered especially in giving a kneading or tapping massage to the shoulder unless the upper kneading ball is pushed out forward when massaging the upper portion of the shoulder of the person to be treated.

An object of the present invention is to provide a massage machine of the chair type wherein massage arms provided with kneading balls can be held inclined forward so as to give a suitable massage.

SUMMARY OF THE INVENTION

To overcome the above problem, the present invention provides a massage machine of the chair type comprising:

- a backrest provided on a chair for the person to be massaged to sit in,
- a massage unit reciprocatingly movable upward and downward longitudinally of the backrest,
- a kneading shaft disposed on the massage unit substantially horizontally and rotatable by a kneading motor,
- pivotal levers supported as inclined on the kneading shaft,
- massage arms supported by forward ends of the respective pivotal levers, and
- kneading balls provided on the respective massage arms each at a position obliquely above the position where the massage arm is supported by the pivotal lever,
- an arm lock mechanism being coupled to the massage unit for holding the kneading balls pushed out forward,
- the arm lock mechanism tiltably supporting arm lock rods each having one end connected to the massage arm at a position away from the position where the massage arm is supported by the pivotal lever,

- each of the arm lock rods being forwardly tiltable by the arm lock mechanism to hold the massage arm with the kneading ball pushed out forward.

With the chair-type massage machine of the present invention, the kneading balls can be held forwardly pushed out by the arm lock mechanism regardless of the intensity of tension of the fabric cover of the backrest. The kneading balls therefore reach the upper portions of the shoulders of the person to be treated to give a highly effective massage.

A finger-pressure massage can be given by pushing out the kneading balls forward by the arm lock mechanism, with the therapeutic fingers in contact with the back, waist or the like.

In order to give a kneading or tapping massage in the usual manner, the kneading balls can be retracted so as not to be forced against the person to be treated.

DESCRIPTION OF THE PREFERRED EMBODIMENTS

The massage machine of the chair type of the invention has a backrest 12 connected as by a frame to the rear end of a seat for the person to be massaged to sit in so as to be tiltable and positionable in place. The backrest 12 is covered with a fabric, cushion or the like. A description will be given below of a massage machine of the chair type wherein not only kneading balls 31, 31 can be held pushed out forward but a massage unit 20 itself is also made tiltable forward or rearward relative to the backrest 12 so that the kneading balls 31, 31 can be pushed out to a greater extent.

Inside Construction of the Backrest

Figure 1:
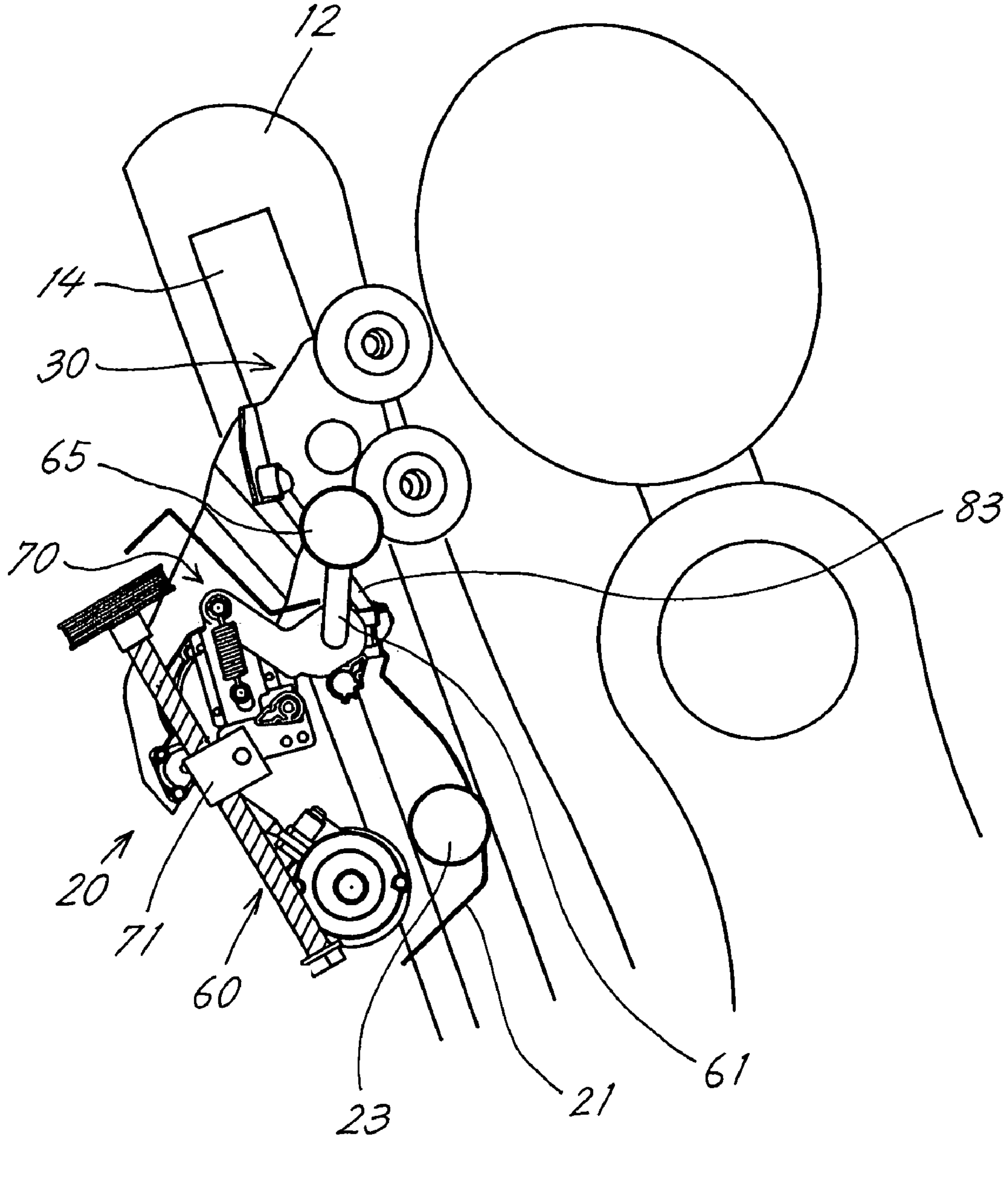
FIG. 1 is a sectional view of a backrest of a massage machine of the chair type.
Figure 2:
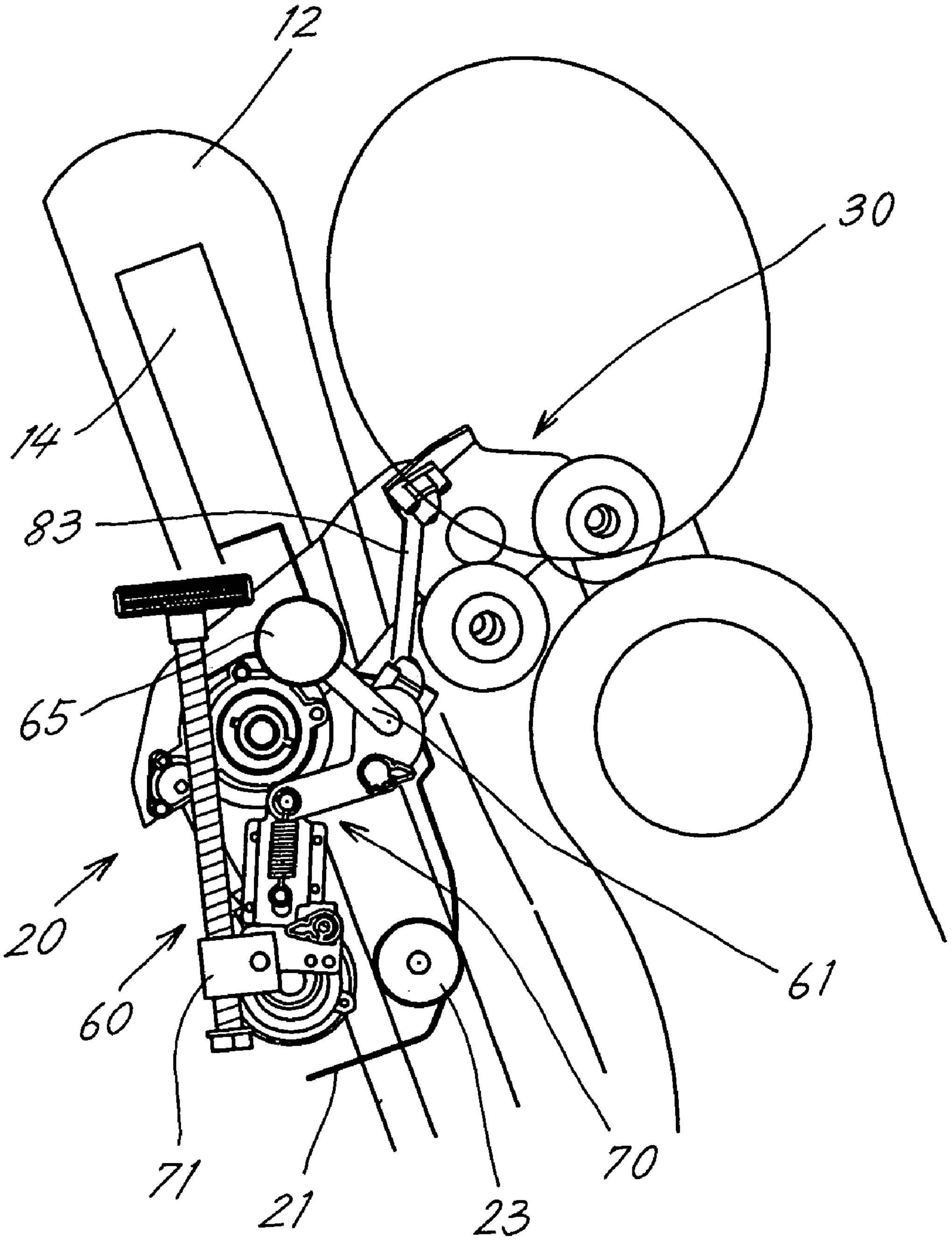
FIG. 2 is a sectional view of the backrest with a massage unit and therapeutic fingers pushed out forward.

As shown in FIGS. 1 and 2, the backrest 12 is provided inside thereof with a pair of opposite guide rails 14 extending upward or downward in parallel longitudinally of the backrest 12. The guide rails 14, 14 are each in the form of a channel and arranged with their grooves opposed to each other. The opening side of each rail 14 has a rack 16 (see FIG. 3). The massage unit 20 to be described later is upwardly or downwardly movably mounted on the guide rails 14, 14.

Figure 3:
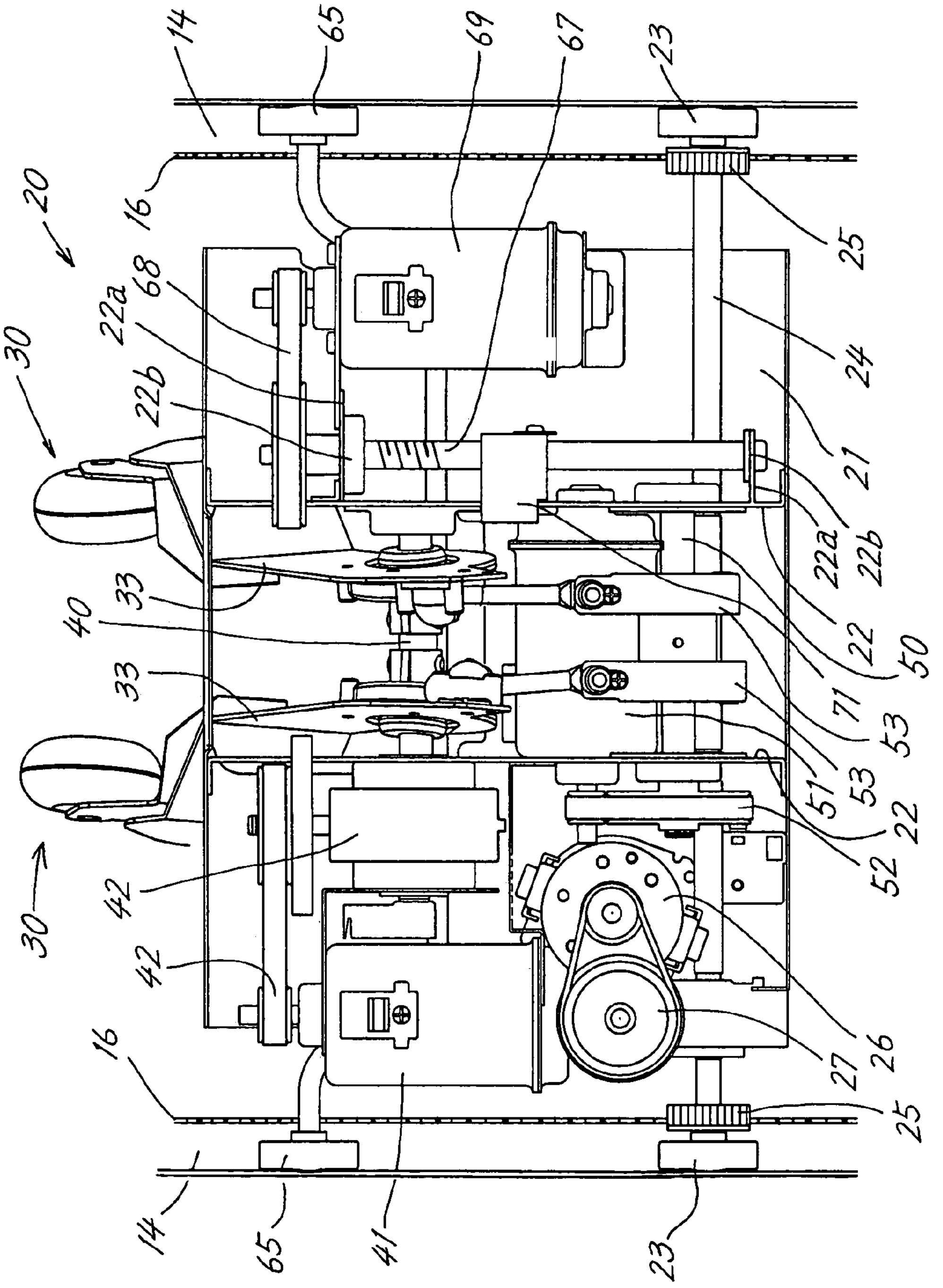
FIG. 3 is a rear view of the massage unit.

With reference to FIGS. 1 to 3, the massage unit 20 has four rollers 23, 23, 65, 65 projecting from a main chassis 21 and fitting in the guide rails 14, 14 and is thereby made movable upward or downward. All components of the massage unit 20 are mounted on the main chassis 21.

Figure 4:
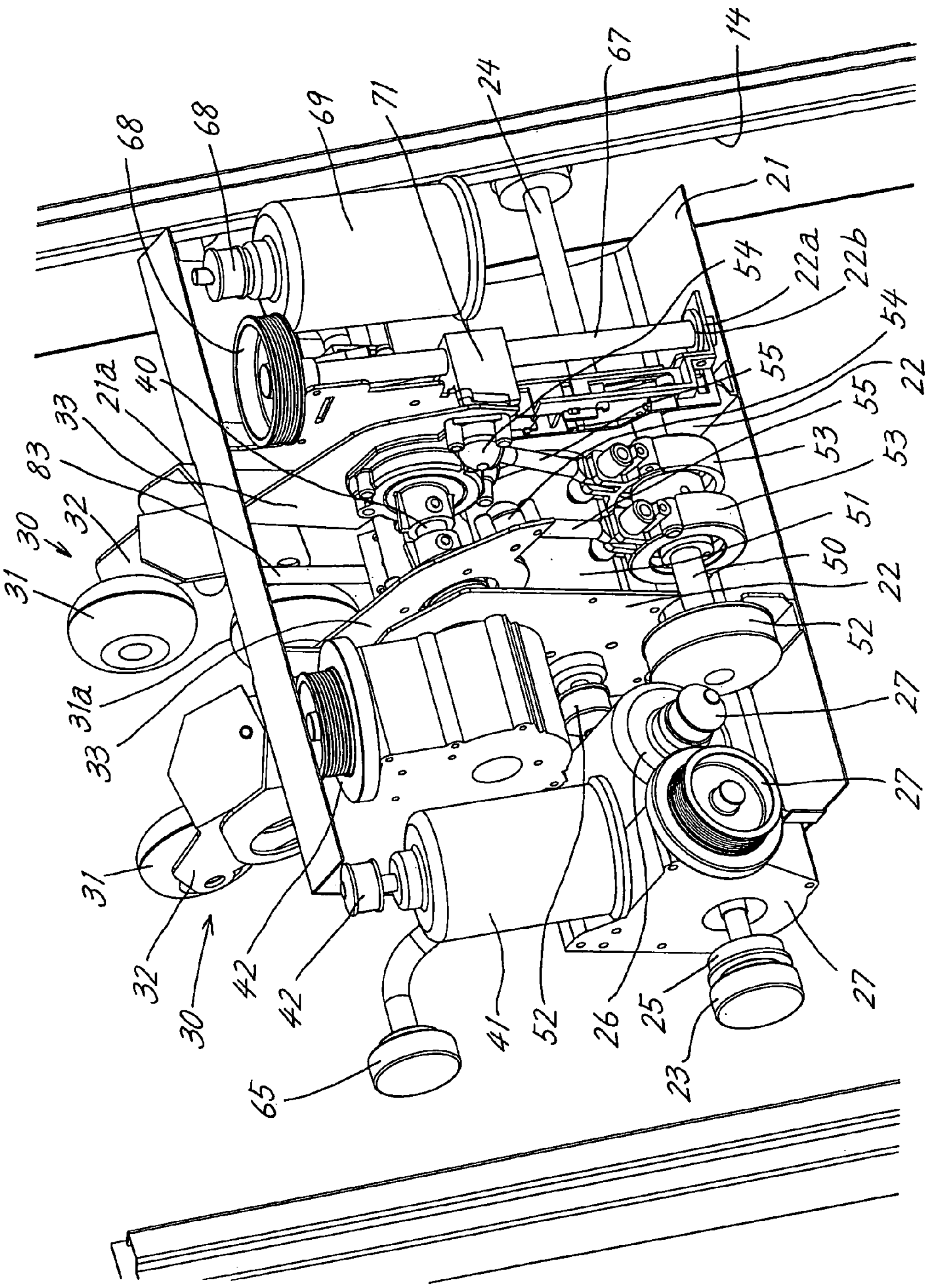
FIG. 4 is a perspective view of the massage unit as it is seen obliquely from behind on the right side thereof.

The main chassis 21 has rear and side openings and is fixedly provided at its center with longitudinal subchassis 22, 22 as spaced apart as shown in FIGS. 3 and 4.

The lower rollers 23, 23 are fitted to opposite ends of a up-and-down rotating shaft 24 extending through lower portions of the subchassis 22, 22 transversely of the machine and projecting from opposite sides of the main chassis 21. Fixedly mounted on the rotating shaft 24 inwardly of the respective rollers 23, 23 are gears 25, 25 meshing with the racks 16, 16 of the guide rails 14, 14. The rotating shaft 24 is coupled to an up-and-down motor 26 via a reduction device 27. The gears 25, 25 meshing with the racks 16, 16 are rotated by driving the motor 26, moving the massage unit 20 upward or downward along the guide rails 14, 14. The combination of pulleys and a belt, or of a worm and worm wheel is usable to provide the reduction device 27. The belt reeved around the pulleys of the reduction device 27 is not shown in FIG. 4.

Construction of Therapeutic Fingers, and Kneading and Tapping Mechanisms

Figure 5:
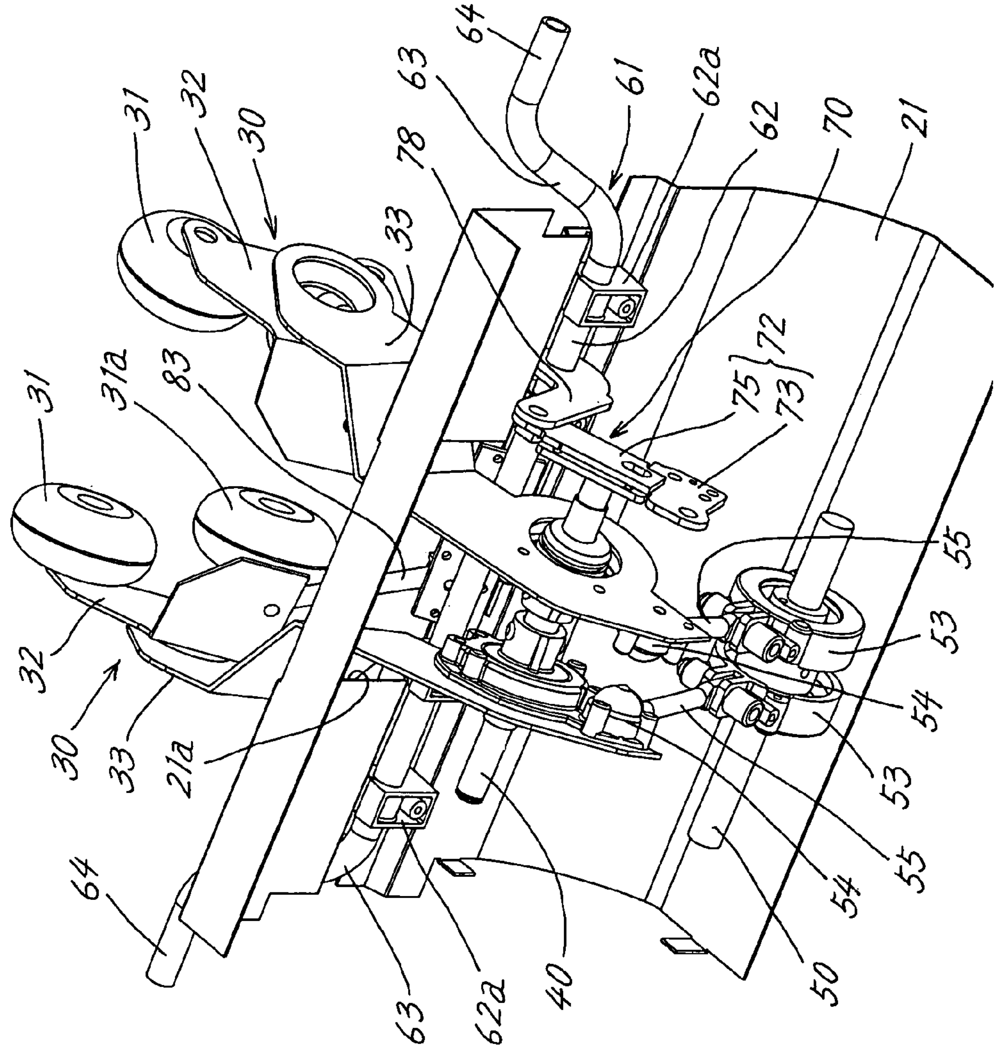
FIG. 5 is a perspective view showing the main components of the massage unit as separated from the machine.

With reference to FIGS. 3 to 5, therapeutic fingers 30, 30 for massaging the person to be treated are coupled to a kneading shaft 40 supported by the subchassis 22, 22 generally centrally thereof and to a tapping shaft 50 supported below the kneading shaft 40. As shown in FIGS. 3 and 4, the kneading shaft 40 and the tapping shaft 50 are coupled to a kneading motor 41 and a tapping motor 51 mounted on the main chassis 21, by way of reduction devices 42, 52, respectively. The combination of pulleys and a belt, or of a worm and worm wheel is usable to provide the reduction device 42 between the kneading shaft 40 and the kneading motor 41. The belt reeved around the pulleys of each of the reduction devices 42, 52 is not shown in FIG. 4.

With reference to FIGS. 4 and 5, the therapeutic fingers 30, 30 each comprise a pivotal lever 33 supported as inclined and positioned eccentrically on the kneading shaft 40 and projecting forward through a hole 21*a* formed in a front wall of the main chassis 21, a massage arm 32 pivoted to the forward end of the pivotal lever 33 and bent at an obtuse angle at the midportion thereof, and kneading balls 31, 31*a* supported respectively at the upper and lower ends of the arm 32.

As shown in FIGS. 4 and 5, eccentric cams 53, 53 which are out of phase with each other by 180 degrees are supported on the tapping shaft 50. Each of the cams 53, 53 is connected by a rod 55 to a universal joint 54 attached to the rear end of the pivotal lever 33 which end is positioned toward the kneading shaft 40.

The pivotal levers 33, 33 are supported as inclined on the kneading shaft 40 and connected to rods 55, 55 and prevented from rotating, so that when the kneading shaft 40 is rotated, the forward ends of the pivotal levers 33, 33 move lefiward and rightward. This movement pivotally moves the massage arms 32, 32 lefiward and rightward, reciprocatingly moving the upper kneading balls 31, 31, as well as the lower kneading balls 31*a*, 31*a*, toward or away from each other repeatedly for a kneading operation.

When the tapping motor 51 rotates, the rods 55, 55 eccentrically connected to the shaft 50 cause the therapeutic fingers 30, 30 to move upward and downward reciprocatingly for a tapping operation.

Pushing-out Mechanism 60

The massage unit 20 is provided with a pushing-out mechanism 60 for moving the unit 20 forward or rearward as shown in FIGS. 1 and 2. The pushing-out mechanism 60 comprises, for example, a crank mechanism 61 and a link mechanism 70 as will be described below.

Figure 6:
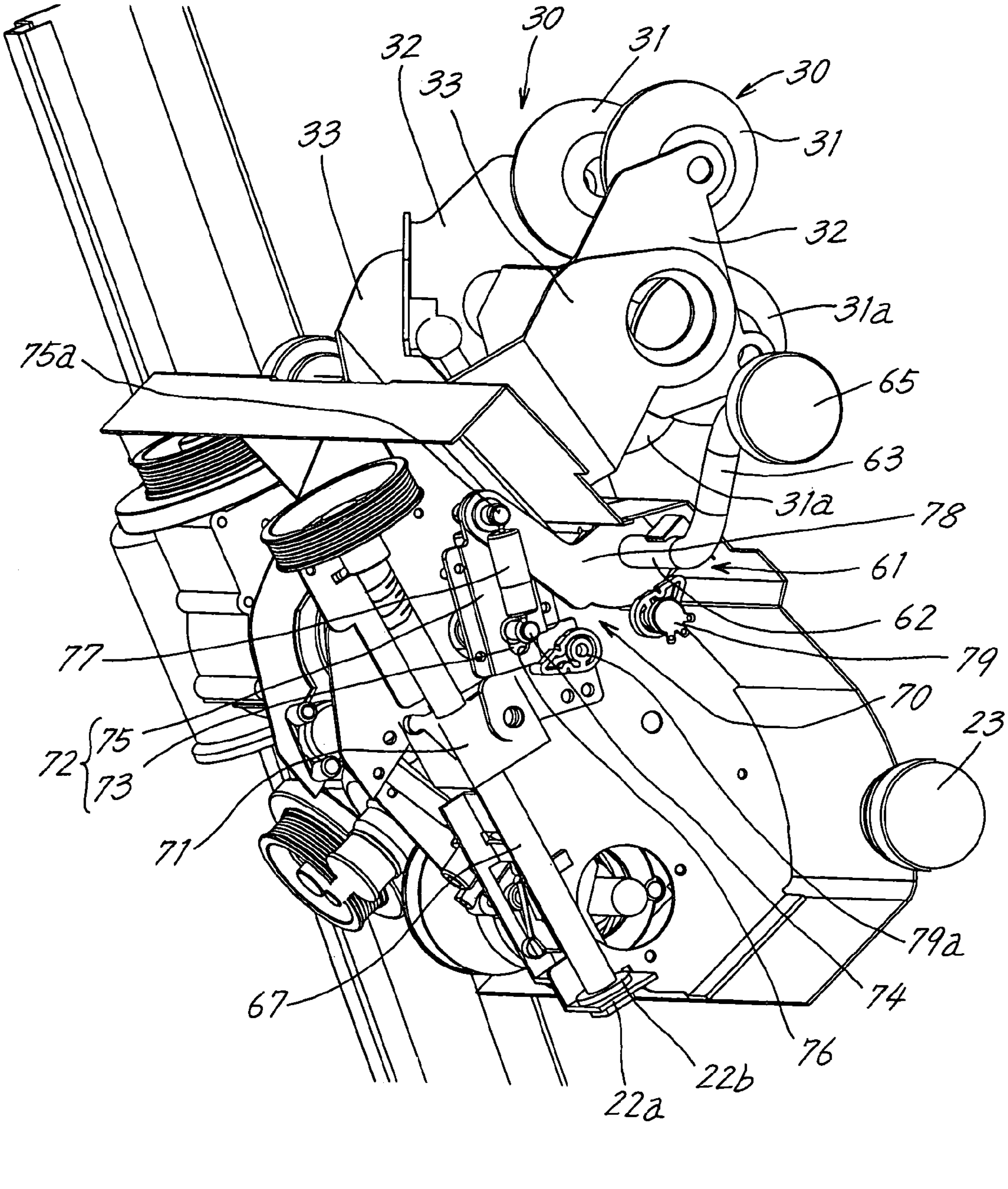
FIG. 6 is a perspective view of the massage unit as it is seen obliquely from behind on the left side thereof.

With reference to FIGS. 5 and 6, the crank mechanism 61 comprises a crankshaft 62 disposed in front of the kneading shaft 40, and crankpins 64, 64 (see FIG. 5) rotatably carrying the upper rollers 65, 65 (see FIG. 6) thereon and connected to the crankshaft 62 by crank arms 63, 63. The crankpins 64, 64 are positioned eccentrically relative to the crankshaft 62, so that when the crankshaft 62 is rotated, the crankpins 64 revolve about the crankshaft 62. With the illustrated embodiment, the crankshaft 62, the crank arms 63, 63 and crankpins 64, 64 are provided by a single metal rod, and the crankshaft 62 is supported on bearings 62*a*, 62*a* by the main chassis 21 as shown in. FIG. 5.

With reference to FIG. 3, the subchassis 22 is provided at upper and lower portions thereof with support pieces 22*a*, 22*a* each having a bearing 22*b*. As shown in FIGS. 3, 4 and 6, a tilting threaded screw rod 67 is supported by the bearings 22*b*, 22*b*. The tilting screw rod 67 has an upper end coupled to a pushing-out motor 69 by way of a reduction device 68 comprising pulleys and a belt (not shown in FIG. 4).

Figure 7:
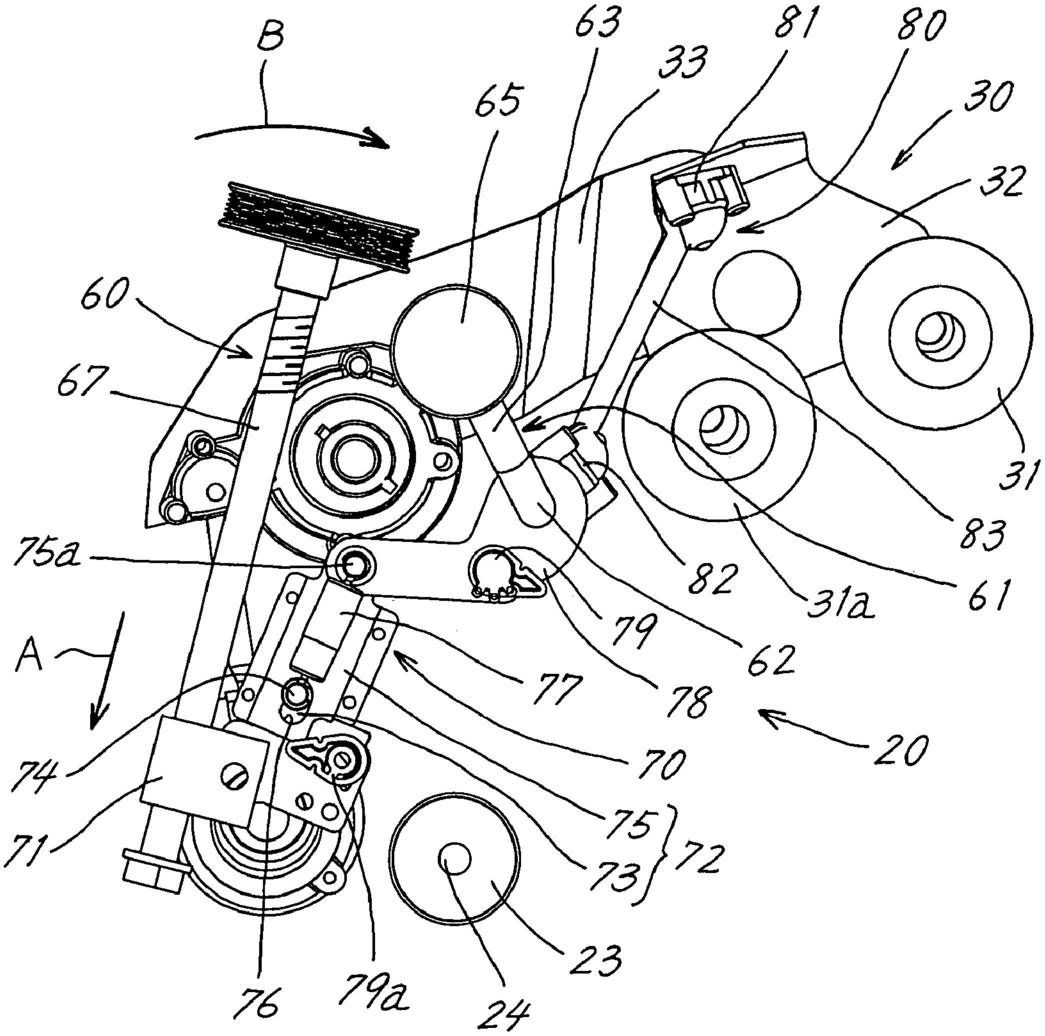
FIG. 7 is a sectional view showing the main components of the massage unit as separated from the machine.

A nut 71 is screw-thread engagement with the threaded portion of the screw rod 67. The nut 71 can be made from a resin. As shown in FIGS. 6 and 7, the link mechanism 70 is connected to the resin nut 71. The link mechanism 70 can be composed of a link 72 and a link piece 78.

The link 72 will be described below with reference to an example of link 72 comprising a first link piece 73 and a second link piece 75 which are slidable relative to each other so as to be contractable longitudinally thereof.

The first link piece 73 is pivoted to the resin nut 71 and tiltable forward or rearward. A slide pin 74 projects from the first link piece 73 in the vicinity of a base end thereof.

The second link piece 75 comprises a pair of members holding the first link piece 73 therebetween and each having a slot 76 extending longitudinally thereof. The slots 76 of the second link piece 75 have slidably fitted therein the slide pin 74 of the first link piece 73.

Further as shown in FIG. 6, the second link piece 75 has a pin 75*a* projecting from the forward end thereof. A spring 77 extends between and is engaged with the slide pin 74 and the pin 75*a*. The spring 77 biases the second link piece 75 toward the resin nut 71. When free of any load, the second link piece 75 is pulled closest to the resin nut 71 by the spring 77.

The link piece 78, i.e., third link piece 78, is supported by the pin 75*a* of the second link piece 75. The third link piece 78 is bent forward at its midportion and has one end secured to the crankshaft 62.

When the resin nut 71 is positioned at an upper portion of the tiling screw rod 67, the third link piece 78 is pulled toward the second link piece 75, bringing the massage unit 20 (main chassis 21) to the most retracted position (see FIG. 1).

When the resin nut 71 is moved down from this position as shown in FIG. 7 (toward the direction of arrow A in FIG. 7) by rotating the tilting screw rod 67, the second link piece 75 pulls down the portion of the third link piece 78 engaging with the piece 75, rotating the third link piece 78 about the crankshaft 62. Since the third link piece 78 is secured to the crankshaft 62, the crankshaft 62 rotates with the third link piece 78.

The crankpins 64, 64 at the opposite ends of the crankshaft 62 are movable only along the guide rails 14, 14 by the rollers 65, 65 and are unable to move forward or rearward, so that the rotation of the crankshaft 62 tilts the massage unit 20 about the up-and-down rotating shaft 24. With the rotating shaft 24 provided below the massage unit 20, the tilting of the unit 20 pushes out the therapeutic fingers 30, 30 forward as shown in FIG. 2 (as indicated by the arrow B in FIG. 7).

By pushing out the fingers 30, 30 at the position of the shoulders of the person to be massaged, the fingers 30, 30 reach the upper portions of the shoulders. The upper portions of the shoulders of the person can be effectively massaged by driving the kneading motor 41 and/or the tapping motor 51 in this state.

When the fingers 30, 30 as positioned at a level lower than the shoulders of the person, i.e., at the position of the back or waist, are pushed out, the back or waist of the person can be massaged with the pressure of the fingers. Further a rolling massage can be given with the fingers 30, 30 pressed against the person to be treated with a great force, by driving the up-and-down motor 26 to move the massage unit 20 upward and downward.

When the tilting screw rod 67 is reversely rotated in the state shown in FIG. 2, the resin nut 71 moves upward to conversely retract the massage unit 20 and pull back the fingers 30, 30 inwardly of the backrest (see FIG. 1). In the retracted state, a massage can be given in the same manner as conventionally.

The amount of pushing-out of the massage unit 20 is controllable by rotating the tilting screw rod 67, namely by adjusting the position of the resin nut 71 relative to the screw rod 67. The maximum amount of pushing-out is also controllable by altering the length of the crank arms 63, 63.

The amount of pushing-out of the massage unit 20 is detectable by pushing-out sensor means 79. As the sensor means 79, for example, a variable resistor 79 is disposed in contact with the third link piece 78 as shown in FIG. 6 to measure variations in the resistance value involved in the angle of rotation of the third link piece 78 by the resistor 79.

The crankshaft 62, which rotates with the third link piece 78, may be provided with the pushing-out sensor means 79.

Other Embodiment of Link Mechanism 70

With the foregoing embodiment, the resin nut 71 is connected to the crankshaft 62 by the link mechanism 70 which comprises the link 72 wherein the second link piece 75 is biased by a spring and slidable relative to the first link piece 73, and the third link piece 78 coupled to the link 72. The first link piece 73 and the second link piece 75 are made slidable relative to each other so as to render the therapeutic fingers 30, 30 (massage unit 20), as pushed out forward, slightly retractable when subjected to a force from the front. Consequently, when the person to be massaged forces his or her back against the backrest 12 with the fingers 30, 30 pushed out, a great rearward force acts on the fingers 30, 30 to retract the massage unit 20. This removes the pain to be otherwise given to the person.

If the above effect need not be produced, the third link piece 78 may be coupled directly to the resin nut 71 by a single piece of link 72 instead of providing separate pieces for use as the first link piece 73 and the second link piece 75.

Since the amount of sliding movement of the second link piece 75 relative to the first link piece 73 corresponds to the force to be applied to the therapeutic fingers 30, 30, means 79*a* can also be provided for detecting the particular part of the body of the person to be massaged with which the fingers 30, 30 are in contact, based on the amount of sliding movement of the second link piece 75. In this case, the amount of sliding movement is detectable by a variable resistor 79*a* or the like which is provided for the first link piece 73 so as to be in contact with the second link piece 75 as shown in FIG. 6.

When the fingers 30, 30 out of contact with the person to be massaged are brought into contact with the shoulders of the person to be massaged, by lowering the massage unit 20 from a position above the backrest 12, an upward force will act on the fingers 30, 30.

As a result, the second link piece 75 slidingly moves upward against the force of the spring 77. The amount of sliding movement of the second link piece 75 is detected by the variable resistor 79*a*. The value of detection indicates that the position if the shoulders of the person.

Arm Lock Mechanism 80

An arm lock mechanism 80 will be described below which serves to project the therapeutic fingers 30, 30 forward with the pushing out of the massage unit 20.

With reference to FIG. 7, the arm lock mechanism 80 comprises arm lock rod 83, 83 each of which couples the bent portion of the massage arm 32 to the crankshaft 62 by universal joint 81, 82. The universal joint 82 for the crankshaft 62 is provided at such a position that when the massage unit 20 is in the most projected position (see FIG. 2), the upper kneading ball 31 on the massage arm 32 can be pushed out to the foremost position. The universal joint 82 is positioned also away from the axis of the crankshaft 62. The universal joint 81 for the massage arm 32 is provided at a position away from the position where the massage arm 32 is supported by the pivotal lever 33.

As the massage unit 20 is pushed out as described above by rotating the crankshaft 62, the universal joint 82 rotates with the rotation of the shaft 62, pushing the arm lock rod 83 upward while tilting the rod. As a result, the arm lock rod 83 rotates the massage arm 32 forward, causing the upper kneading ball 31 to project forward relative to the main chassis 21 from a state in which the upper and lower kneading balls 31, 31*a* are generally in parallel to the backrest 12.

In addition to the pushing-out of the massage unit 20 by the pushing-out mechanism 60 described, the kneading ball 31 is thus pushed out greatly to the upper portion of the shoulder to massage the shoulder effectively.

A massage can be given by kneading and/or tapping with the upper kneading balls 31 thus projected, by rotating the kneading shaft 40 and/or the tapping shaft 50 in this state.

When the above operation is performed with the therapeutic fingers 30, 30 in bearing contact with the back or waist of the person to be massaged, a finger-pressure massage can also be given by the upper kneading balls 31.

Further when the massage unit 20 is retracted by rotating the crankshaft 62 reversely, each universal joint 82 pulls the arm lock rod 83 downward conversely to the above movement. As a result, the arm lock rod 83 rotates the massage arm 32 rearward to return the upper and lower kneading balls 31, 31*a* to the position generally in parallel to the backrest 12 for the balls to perform a massage in the usual manner.

Apparently, the present invention can be modified or altered by one skilled in the art without departing from the spirit of the invention, and such modifications are included within the scope of the invention as set forth in the appended claims.

The invention claimed is:

1. A massage machine comprising:

a backrest provided on a chair for the person to be massaged to sit in, a massage unit reciprocatingly movable upward and downward longitudinally of the backrest, a kneading shaft disposed on the massage unit substantially horizontally and rotatable by a kneading motor, pivotal levers supported as inclined on the kneading shaft, massage arms supported by forward ends of the respective pivotal levers, and kneading balls provided on the respective massage arms each at a position obliquely above the position where the massage arm is supported by the pivotal lever, an arm lock mechanism coupled to the massage unit for holding the kneading balls pushed out forward, the arm lock mechanism tiltably supporting arm lock rods each having one end connected to the massage arm at a position away from the position where the massage arm is supported by the pivotal lever, each of the arm lock rods being forwardly tiltable by the arm lock mechanism to hold the massage arm with the kneading ball pushed out forward.

2. The massage machine according to claim 1 wherein the arm lock mechanism comprises a rotatable shaft, and the arm lock rods are connected to the shaft each at a position away from the center of rotation of the shaft.

3. The massage machine according to claim 2 wherein each of the arm rock rods is connected to the massage arm and the shaft by respective universal joints.

4. The massage machine according to claim 1 wherein the massage arm is bent at an obtuse angle, supported at the bent portion by the pivotal lever and provided with kneading balls respectively at upper and lower ends thereof, the massage arm being forwardly tiltable by the arm lock mechanism to push out the upper kneading ball forward and hold the upper kneading ball pushed out forward.

* * * * *